(12) United States Patent
Evison et al.

(10) Patent No.: US 7,544,349 B2
(45) Date of Patent: Jun. 9, 2009

(54) PERSONAL CARE COMPOSITIONS

(75) Inventors: Jane Evison, Nottingham (GB); Janet Palin, Nottingham (GB); Edward Galley, Nottingham (GB)

(73) Assignee: The Boots Company, PLC, Nottingham (GB)

( * ) Notice: Subject to any disclaimer, the term of this patent is extended or adjusted under 35 U.S.C. 154(b) by 490 days.

(21) Appl. No.: 10/486,572

(22) PCT Filed: Jul. 31, 2002

(86) PCT No.: PCT/GB02/03490

§ 371 (c)(1),
(2), (4) Date: Feb. 11, 2004

(87) PCT Pub. No.: WO03/013456

PCT Pub. Date: Feb. 20, 2003

(65) Prior Publication Data

US 2004/0241112 A1 Dec. 2, 2004

(30) Foreign Application Priority Data

Aug. 11, 2001 (GB) ................................. 0119645.0

(51) Int. Cl.
*A61K 8/00* (2006.01)
*A61K 31/60* (2006.01)
*A61K 31/21* (2006.01)
*A61K 31/045* (2006.01)
*A61Q 17/04* (2006.01)
*A01N 37/36* (2006.01)
*A01N 37/00* (2006.01)

(52) U.S. Cl. ............................ 424/59; 424/60; 514/159; 514/163; 514/506; 514/730

(58) Field of Classification Search ................... 424/59, 424/60; 514/159, 163, 506, 730
See application file for complete search history.

(56) References Cited

U.S. PATENT DOCUMENTS

| 3,419,366 A | 12/1968 | Mitchell et al. |
| 4,168,248 A | 9/1979 | Kulka |
| 4,323,694 A | 4/1982 | Scala, Jr. |
| 5,667,765 A | 9/1997 | Hansenne et al. |
| 6,706,674 B2 * | 3/2004 | Cincotta et al. ............. 510/119 |

FOREIGN PATENT DOCUMENTS

| DE | 38 24 999 A | 2/1989 |
| EP | 0 787 483 A | 8/1997 |
| EP | 0 930 063 | * 7/1999 |
| EP | 0 930 063 A | 7/1999 |

* cited by examiner

*Primary Examiner*—Ernst V Arnold
(74) *Attorney, Agent, or Firm*—Rothwell, Figg, Ernst & Manbeck, P.C.

(57) ABSTRACT

There are described personal care compositions containing a) one or more dibenzoylmethane sunscreening agents; and b) a photostablising amount of a salicylate ester of formula (1): (2-OH)Ph-(CO)—O—R, wherein R represents an alkyl group consisting of a chain of from 7 to 16 carbon atoms substituted by at least one group selected from methyl and ethyl. The compound of formula (1) is preferably isodecyl salicylate or isotridecyl salicylate. The salicylate esters of formula (1) have a stabilizing effect on the compositions. The salicylate esters prevent or inhibit degradation of the sunscreening agents which would otherwise lead to a reduction in the efficacy of the sunscreening agents and an increase in the deleterious effects of exposure to sunlight on the user of the compositions or on the compositions themselves.

28 Claims, No Drawings

PERSONAL CARE COMPOSITIONS

CROSS REFERENCE TO RELATED APPLICATION

This application is a 35 USC § 371 National Phase Entry Application from PCT/GB02/03490, filed Jul. 31, 2002, and designating the U.S.

The present invention relates to personal care compositions containing sunscreening compounds to counteract the deleterious effects of UV radiation. In one aspect of the present invention the personal care compositions are sunscreen compositions in which a sunscreening compound is used to protect the user's skin or hair from UV radiation. The term "sunscreen composition" is used herein to encompass sunscreening compositions such as moisturisers, day creams, colour cosmetics including foundations, lipsticks, eye shadows, blushers etc, tanning lotions and sunblockers, and toiletry products such as shower gels, shampoos and conditioners, which are intended for topical application to provide protection for the skin or hair against the sun's rays or other sources of ultraviolet (UV) radiation. Such sunscreen compositions may contain additional inorganic or organic sunscreening agents. In a further aspect of the present invention the personal care compositions are cosmetic/toiletries compositions containing a sunscreening compound to protect the compositions from the deleterious effects of exposure of the compositions to UV radiation. The term "cosmetic/toiletries composition" is used herein to encompass compositions intended for application to the skin or hair in which the sunscreen compounds are present to protect the compositions from the deleterious effects of exposure of the composition to UV radiation. Examples of cosmetic/toiletries composition include gels such as bath gels or shower gels, shampoos optionally containing conditioning agents and/or antidandruff agents, hair conditioners, liquid soaps, creams and lotions. Such compositions may be emulsions (oil-in-water emulsions or water-in-oil emulsions).

A commonly used group of sunscreening compounds are the dibenzoylmethanes, particularly 4-(1,1-dimethylethyl)-4'-methoxydibenzoyl methane (available commercially under the trade name PARSOL 1789) and 4-isopropyldibenzoylmethane (available commercially under the trade name EUSOLEX 8020). It is well known to those skilled in the art that dibenzoylmethanes whether used on their own or in combination with other sunscreening agents tend to photodegrade when exposed to UV radiation. This degradation reduces the efficacy of the sunscreening compound. The protection from the deleterious effects of exposure to sunlight being enjoyed by the user who has applied a sunscreening composition to their skin or hair is thereby reduced. The protection for compositions which contain sunscreening agents to protect the compositions against the deleterious effects of exposure to UV radiation is also reduced.

The present invention provides personal care compositions containing
a) one or more dibenzoylmethane sunscreening agents; and
b) a photostabilising amount of a salicylate ester of formula I (2-OH)Ph-(CO)—O—R    I wherein R represents an alkyl group consisting of a chain of from 7 to 16 carbon atoms substituted by at least one group selected from methyl and ethyl.

The group R may be represented by the generic structure Ia:

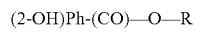

wherein n represents an integer from 7 to 16, m is 1 or more, and each group Sub independently represents a methyl or an ethyl group.

Preferably, m is an integer of between 1 and 4.

Where m is greater than 1, ie when there is more than one methyl and/or ethyl substituent on the alkyl chain, those methyl and/or ethyl groups may be attached to the same or different carbon atoms of the alkyl chain.

Where m is greater than 1, it is preferred that all the Sub groups in the molecule of formula I are the same, ie the Sub groups are either all methyl groups or all ethyl groups.

We particularly prefer compounds of formula I in which Sub represents methyl and m is from 1 to 4, particularly 3.

We particularly prefer compounds of formula I in which Sub represents ethyl and m is from 1 to 4, particularly 1.

Another preferred group of compounds are those in which n represents 7 to 12, particularly 7 to 10.

The group R preferably contains between 8 and 16 carbon atoms in total, more preferably between 9 and 14 carbon atoms, eg 10 or 13 carbon atoms.

Particular compounds of formula I that may be mentioned are isodecyl salicylate, in which R represents a 7-carbon chain substituted by 3 methyl groups, and isotridecyl salicylate, in which R represents an 11-carbon chain substituted by an ethyl group.

Compounds of formula I may all be used in the form of mixtures. Also, the compounds of formula I may be present in two or more isomeric forms. Thus, for instance, isodecyl salicylate may comprise molecules in which the three methyl groups are present at various positions on the alkyl chain. In such cases, a single molecular species may predominate, or two or more species may both be present in substantial proportions.

As used herein, the terms "dibenzoylmethane" and "dibenzoylmethane sunscreening agent" are used generically to encompass any and all sunscreening agent(s) present in the composition that have a dibenzoylmethane grouping in their structure, irrespective of the nature of any substituents on that grouping. Examples of dibenzoylmethane sunscreening agents are 4-(1,1-dimethylethyl)-4'-methoxydibenzoyl methane (also known as butylmethoxy dibenzoylmethane) and 4-isopropyldibenzoylmethane. A particularly preferred dibenzoylmethane sunscreening agent is 4-(1,1-dimethylethyl)-4'-methoxydibenzoyl methane.

In addition to the dibenzoylmethane sunscreening agent(s), the compositions according to the invention may optionally include additional sunscreening agents.

The personal care compositions of the present invention may contain a total 0.05 to 20% of sunscreening agent(s) by weight of the total composition. In compositions intended to be applied to the skin or hair to protect the skin or hair from the deleterious effects of exposure to UV radiation, the total amount of sunscreening agent(s) that may be present is preferably in the range 0.5 to 10%, more preferably 1 to 6%. In compositions in which the sunscreening agent(s) are present to protect the compositions from the deleterious effects of exposure to UV radiation, the total amount of sunscreening agent(s) that may be present is preferably less than 1% by weight of the total composition, more preferably 0.05 to 0.6%, most preferably 0.3 to 0.5%.

The personal care compositions of the present invention may contain a total of 0.05 to 10% of dibenzoylmethane by weight of the total composition. In compositions intended to be applied to the skin or hair to protect the skin or hair from the deleterious effects of exposure to UV radiation, the amount of dibenzoylmethane that may be present is preferably in the range 0.5 to 10%, more preferably 1 to 6%. In

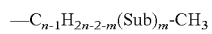

compositions in which the dibenzoylmethane is present to protect the compositions from the deleterious effects of exposure to UV radiation, the amount of dibenzoylmethane that may be present is preferably less than 1% by weight of the total composition, more preferably 0.05 to 0.6%, most preferably 0.3 to 0.5%.

The personal care compositions of the present invention may contain 0.1 to 30% by weight of the salicylate ester of formula I, preferably 1 to 25%, more preferably 4 to 20%.

Examples of suitable additional inorganic sunscreening agents include:
a) Microfine titanium dioxide;
b) Microfine zinc oxide; and
c) Boron nitride.

Examples of suitable additional organic sunscreening agents include:
a) p-aminobenzoic acids, esters and derivatives thereof, for example, 2-ethylhexyl p-dimethylaminobenzoate and the octyl ester of p-aminobenzoic acid;
b) methoxycinnamate esters such as 2-ethylhexyl p-methoxycinnamate, 2-ethoxyethyl p-methoxycinnamate or $\alpha,\beta$-di-(p-methoxycinnamoyl)-$\alpha'$-(2-ethylhexanoyl)-glycerin;
c) benzophenones such as oxybenzone;
d) 2-phenylbenzimidazole-5-sulfonic acid and disodium phenyl dibenzimidazole tetrasulfonate and terphthalylidene dicamphor sulfonic acid;
e) alkyl-$\beta,\beta$-diphenylacrylates for example alkyl $\alpha$-cyano-$\beta,\beta$-diphenylacrylates such as octocrylene;
f) triazines such as 2,4,6-trianilino-(p-carbo-2ethylhexyl-1'-oxy)-1,3,5 triazine and bis-octyloxyphenol methoxyphenyl triazine;
g) camphor derivatives such as methylbenzylidene camphor;
h) organic pigment sunscreening agents such as methylene bis-benzotriazole tetramethyl butylphenol;
i) silicone derivatives such as drometrizole trisiloxane and benzylidene malonate polysiloxane;
k) salicylates such as octyl salicylate.

Any additional sunscreening agent may be present in an amount of 0.1 to 10% by weight of the composition.

Example formulations include shampoos containing conditioning agents and pearlescent systems, hair conditioners, serums, creams, and lotions. Such compositions may be emulsions (oil-in-water or water-in-oil).

The personal care compositions of the present invention may be sunscreen products such as aqueous or oily solutions or dispersions or emulsions in the conventional way. The emulsion may be an oil-in-water emulsion or a water-in-oil emulsion.

The oil phase of the water-in-oil or oil-in-water emulsions of the present invention may comprise for example:
a) hydrocarbon oils such as paraffin or mineral oils;
b) waxes such as beeswax or paraffin wax;
c) natural oils such as sunflower oil, apricot kernel oil, shea butter or jojoba oil;
d) silicone oils such as dimethicone, cyclomethicone or cetyidimethicone;
e) fatty acid esters such as isopropyl palmitate, isopropyl myristate or dioctylmaleate;
f) fatty alcohols such as cetyl alcohol or stearyl alcohol; or
g) mixtures thereof, for example, the blend of waxes available commercially under the trade name Cutina (Henkel).

In preferred water-in-oil compositions of the present invention the oil phase comprises 5 to 40%, more preferably 10 to 30% by weight of the composition. In preferred oil-in-water compositions of the present invention the oil phase comprises 5 to 30%, more preferably 10 to 20% by weight of the composition.

The emulsifiers used may be any emulsifiers known in the art for use in water-in-oil or oil-in-water emulsions. It has been found that particularly effective water-in-oil and oil-in-water sunscreen compositions can be prepared by using an emulsifier or mixture of emulsifiers selected from known cosmetically acceptable emulsifiers which include:
a) sesquioleates such as sorbitan sesquioleate, available commercially for example under the trade name Arlacel 83 (ICI), or polyglyceryl-2-sesquioleate;
b) ethoxylated esters of derivatives of natural oils such as the polyethoxylated ester of hydrogenated castor oil available commercially for example under the trade name Arlacel 989 (ICI);
c) silicone emulsifiers such as silicone polyols available commercially for example under the trade name ABIL WS08 (Th. Goldschmidt AG);
d) anionic emulsifiers such as fatty acid soaps e.g. potassium stearate and fatty acid sulphates e.g. sodium cetostearyl sulphate available commercially under the trade name Dehydag (Henkel);
e) ethoxylated fatty alcohols, for example the emulsifiers available commercially under the trade name Brij (ICI);
f) sorbitan esters, for example the emulsifiers available commercially under the trade name Span (ICI);
g) ethoxylated sorbitan esters, for example the emulsifiers available commercially under the trade name Tween (ICI);
h) ethoxylated fatty acid esters such as ethoxylated stearates, for example the emulsifiers available commercially under the trade name Myrd (ICI);
i) ethoxylated mono, di-, and triglycerides, for example the emulsifiers available commercially under the trade name Labrafil (Alfa Chem.);
j) non-ionic self-emulsifying waxes, for example the wax available commercially under the trade name Polawax (Croda);
k) ethoxylated fatty acids, for example, the emulsifiers available commercially under the trade name Tefose (Alfa Chem.);
l) methylglucose esters such as polyglycerol-3 methyl glucose distearate available commercially under the name Tegocare 450 (Degussa Goldschmidt); or
m) mixtures thereof.

The amount of emulsifier present in the emulsion compositions of the present invention is preferably in the range 1 to 10%.

The compositions of the present invention may additionally comprise other components which will be well known to those skilled in the art. These include, for example, emollients such as isopropyl myristate or triglycerides of fatty acids e.g. lauric triglyceride or capric/caprylic triglyceride, such as the triglyceride available commercially under the trade name Miglyol 810 (Huls UK); moisturisers such as D-panthenol; humectants such as glycerin or 1,3-butylene glycol; antioxidants such as DL-$\alpha$-tocopherylacetate or butylated hydroxytoluene; emulsion stabilising salts such as sodium chloride, sodium citrate or magnesium sulphate; film formers to assist spreading on the surface of the skin such as alkylated polyvinylpyrrolidone, e.g. those available commercially under the trade name Antaron (GAF); thickeners such as acrylic acid polymers, e.g. those available commercially under the trade name Carbopol (B.F. Goodrich) or modified celluloses, e.g. hydroxyethylcellulose available commercially under the trade name Natrosol (Hercules) or alkylgalactomanans available under the trade name N-Hance; preservatives such as bronopol, sodium dehydroacetate, polyhexamethylenebiguanide hydrochloride, isothiazolone or diazolidinylurea; sequestering agents such as EDTA salts; perfumes and colourings.

The personal care compositions of the present invention are advantageous primarily in that the presence of the salicylate esters of Formula I has been found to have a stabilizing effect on the compositions. The salicylate esters prevent or inhibit degradation of the sunscreening agents which would otherwise lead to a reduction in the efficacy of the sunscreening agents and an increase in the deleterious effects of exposure to sunlight on the user of the compositions or on the compositions themselves.

The stability of the compositions according to the invention upon exposure to sunlight or other sources of UV light (photostability) may be measured by the following method:

Photostability Measurement

A smooth quartz slide (2.5 cm×2.5 cm) was cleaned with denatured alcohol which was allowed to evaporate off. The clean slide was then weighed to 1 µg accuracy. This slide was then coated with "cling film", ensuring that no air bubbles were trapped. A hole (1.5 cm×1.5 cm) was then cut in the centre of the cling film. The slide was then gently cleansed, using a tissue with denatured alcohol.

The sample was then applied to one edge of the recess cut in the cling film using a positive displacement micropipette. The sample was then drawn down over the recess, with a clean flat edge of another slide, so as to fill the well with product, producing an even, 20-micron deep layer (with no air bubbles). The cling film was then removed and the slide reweighed. The sample was then left to dry for 15 minutes.

Using a xenon lamp (which had previously being calibrated against a standard sunlight spectrum as defined by COLIPA), samples on the quartz were exposed for different time durations (10, 20, 30 and 60 minutes). To calculate the changes in photostability, spectral absorbance values were used. Transmission values are measured for the treated and untreated slides at wavelengths 290 nm to 400 nm at 5 nm increments. Transmission readings are converted to absorbance units. A graph of wavelength vs absorbance is calculated for each of the time intervals and the area under the curve is calculated. These values are then plotted on a graph of cumulative absorbance versus time. The percentage photostability of the product for up to 60 minutes was calculated using the following equation:

Percentage photostability=60 min cumulative absorbance/zero cumulative absorbance×100

Using the above method, the photostability was measured for a standard sunscreen base (Control) and for two formulations of the same base containing 4% isotridecyl salicylate and 4% isodecyl salicylate respectively. The results are set out in Table 1:

TABLE 1

| Sample | Additive Trade Name | Additive Supplier | % Photostability |
|---|---|---|---|
| Control | — | — | 72.5 |
| +4% Isotridecyl salicylate | Cosmocol ESI | Pointings | 81.0 |
| +4% Isodecyl salicylate | Keratoplast | Paroxite | 81.9 |

The efficacy of the compositions of the invention may be assessed in terms of the Sun Protection Factor (SPF). The SPF is defined as the minimum dose of UV radiation required to show the first signs of burning or reddening of protected skin divided by the minimum dose for unprotected skin. The SPF may thus be measured in vivo by comparative measurements on volunteers under standardized conditions, eg the COLIPA industry-standard method. Another measure of the usefulness of a sunscreening product is the spectral width over which it is effective. This may be assessed in terms of industry standards such as the Boots Star Rating System, which is the ratio of the mean absorbance in the UVA region (around 280-320 nm) to the mean absorbance in the UVB region (320-400 nm). A method for the determination of the star rating of a composition, which also gives an in vitro indication of the likely SPF, is as follows:

Measurement of Star Rating and in vitro SPF

The method is an in-vitro assay conducted to measure the UVA/UVB absorbance ratio of a sunscreen product, to determine its star rating. It is based on a published method by Diffey and Robson ["A new substrate to measure sunscreen protection factors throughout the ultraviolet spectrum" BL Diffey and J Robson, J Soc Cosmet Chem, 40, 127-133 (May/June 1989)]. The UVA/UVB ratio is an indicator of the UVA absorbance properties of a sunscreen product, relative to UVB absorbance properties which enables classification for the star rating system. The higher the star rating the greater the ratio of UVA:UVB absorbance, a ratio of 0.8 or greater being classified as "4-star", 0.60 to 0.79 as "3-star", 0.40 to 0.59 as "2-star" and 0.20 to 0.39 as "1-star".

An SPF 290S analyser system was calibrated and optimised to ensure the maximum signal over the required 290 to 400 nm wavelength range, according to the operation manual. A blank UV transpore™ surgical tape is scanned as a reference to determine 100% transmission of UV light (290 nm-400 nm). The sunscreen product is applied at a rate of 2 mg/cm$^2$ to transpore tape. The product is applied and is spread evenly over a total area of 114 cm$^2$. The product is then left to dry for 10 minutes prior to scanning. The tape with sunscreen on is then scanned in 12 different locations. A scan consists of UV transmission measurements taken at 5 nm increments from 290 to 400 nm. At least 5 separate scans should be performed from which a mean star rating and in-vitro SPF can be calculated.

The invention will be illustrated by the following Examples which are given by way of example only. All percentages are by weight of the final composition.

The Examples utilise one or both of the typical salicylates in Table 2:

TABLE 2

Isotridecyl salicylate
Isodecyl salicylate

EXAMPLE 1

The following components are used to make a sunscreen composition of the present invention.

| | Ingredient | % |
|---|---|---|
| 1 | One or combination of the salicylates in Table 2 | 10.0 |
| 2 | Diglyceryl esters | 5.3 |
| 3 | Silicone fluid 1000 | 4.8 |
| 4 | Microcrystalline wax | 1.9 |
| 5 | Ceareth 2 phosphate | 1.0 |
| 6 | Cetyl alcohol | 0.48 |

-continued

| | Ingredient | % |
|---|---|---|
| 7 | Almond oil | 0.48 |
| 8 | Butylmethoxy dibenzoyl methane | 2.9 |
| 9 | Octyl methoxycinnamate | 1.9 |
| 10 | Octocrylene | 8.00 |
| 11 | Butylated hydroxytoluene | 0.05 |
| 12 | Acrylates cross polymer | 0.4 |
| 11 | Tetrapropoxy ethylenediamine | 1.1 |
| 14 | 1,3-Butylene glycol | 4.8 |
| 15 | Preservative | qs |
| 16 | Water | to 100% |

Method
A Ingredients 1 to 11 are mixed and heated to 65° C. to melt together.
B Ingredients 12 to 16 are mixed and heated to 70° C.
C Part A is added to part B slowly with stirring.
D Homogenise for 20 minutes to give sunscreen compositions having an SPF of 25.

EXAMPLE 2

The following components are used to make a sunscreen composition of the present invention.

| | Ingredient | % |
|---|---|---|
| 1 | One combination of the salicylates in Table 2 | 21.0 |
| 2 | Silicone fluid 1000 | 2.0 |
| 3 | Microcrystalline wax | 1.9 |
| 4 | Ceteareth 2 phosphate | 1.0 |
| 5 | Cetyl Alcohol | 0.48 |
| 6 | Butylmethoxydibenzoyl methane | 2.9 |
| 7 | Octyl methoxycinnamate | 1.9 |
| 8 | Octocrylene | 8.00 |
| 9 | Butylated Hydroxytoluene | 0.048 |
| 10 | Acrylates cross polymer | 0.4 |
| 11 | Tetrapropoxy ethylenediamine | 1.1 |
| 12 | 1,3-Butylene Glycol | 4.8 |
| 13 | Preservative | qs |
| 14 | Water | to 100 |

Method
A Ingredients 1 to 9 are mixed and heated to 65° C. to melt together.
B Ingredients 10 to 14 are mixed and heated to 70° C.
C Part A is added to part B slowly with stirring.
D Homogenise for 20 minutes to give sunscreen compositions having an SPF of 25.

EXAMPLE 3

The following components are used to make a sunscreen composition of the present invention.

| | Ingredient | % |
|---|---|---|
| 1 | One or combination of the salicylates in Table 2 | 20 |
| 2 | Silicone Fluid 1000 | 2.0 |
| 3 | Microcrystalline Wax | 2 |
| 4 | Ceteareth 2 phosphate | 1 |
| 5 | Cetyl Alcohol | 0.5 |
| 6 | Butylmethoxy dibenzoyl methane | 3 |
| 7 | Methylene bis-benzotriazole tetramethyl butylphenol | 0.2 |
| 8 | Octyl methoxy cinnamate | 2 |
| 9 | Butylated Hydroxytoluene | 0.05 |
| 10 | Acrylates cross polymer | 0.4 |
| 11 | Tetrapropoxy ethylenediamine | 1.2 |
| 12 | 1,3-Butylene Glycol | 5 |

-continued

| | Ingredient | % |
|---|---|---|
| 13 | Preservative | qs |
| 14 | Water | to 100 |

Method
A Ingredients 1 to 6, and 8 and 9 are mixed and heated to 65° C. to melt together.
B Ingredients 7, 10 to 14 are mixed and heated to 70° C.
C Part A is added to part B slowly with stirring.
D Homogenise for 20 minutes to give sunscreen compositions having an SPF of 25.

EXAMPLE 4

The following components are used to make a sunscreen composition of the present invention.

| | Ingredient | % |
|---|---|---|
| 1 | C12-C15 Alcohols Benzoate | 4 |
| 2 | One or combination of the salicylates in Table 2 | 4 |
| 3 | Octyl methoxycinnamate | 1 |
| 4 | Butylmethoxy dibenzoyl methane | 1.50 |
| 5 | Silicone Fluid 1000 | 2 |
| 6 | Microcrystalline Wax | 1 |
| 7 | DL-A-Tocopheryl Acetate | 0.2 |
| 8 | PVP/Hexadecene Copolymer | 1.75 |
| 9 | Glyceryl-3 Glucose Distearate | 2 |
| 10 | Acrylates/Vinyl Ester Copolymer | 0.15 |
| 11 | Triclosan | 0.19 |
| 12 | 1,3-Butylene Glycol | 5 |
| 13 | Sequestrene NA4 | 0.02 |
| 14 | Caustic Potash Soln 45% w/w | 0.068 |
| 15 | Preservative | qs |
| 16 | Water | to 100 |

Method
A Ingredients 1 to 9 are mixed and melted together at 65° C.
B Ingredients 10, 11, 12, 13, 14, 15, are dissolved into 16 and heated to 65° C.
C Part A is added to part B with stirring and homogenised for 20 minutes to give sunscreen compositions having an SPF of 8.

EXAMPLE 5

The following components are used to make a sunscreen composition of the present invention.

| | Ingredient | % |
|---|---|---|
| 1 | One or combination of the salicylates in Table 2 | 15.0 |
| 2 | Octyl methoxycinnamate | 3.8 |
| 3 | Butylmethoxy dibenzoyl methane | 3.0 |
| 4 | Silicone Fluid 1000 | 0.5 |
| 5 | Microcrystalline Wax | 1.5 |
| 6 | DL-A-Tocopheryl Acetate | 0.2 |
| 7 | PVP/Hexadecene Copolymer | 1.75 |
| 8 | Triclosan | 0.20 |
| 9 | Butylated Hydroxytoluene BP | 0.05 |
| 10 | Glyceryl-3 Glucose Distearate | 2.00 |
| 11 | Acrylates/Vinyl Ester Copolymer | 0.14 |
| 12 | Titanium Dioxide T 805 | 0.30 |
| 13 | Sequestrene NA4 | 0.02 |
| 14 | 1,3-Butylene Glycol | 5.00 |
| 15 | Sorbithom TEP | 0.50 |
| 16 | Caustic Potash Soln 45% w/w | 0.07 |

-continued

| | Ingredient | % |
|---|---|---|
| 17 | Preservative | qs |
| 18 | Water | to 100 |

Method

A Ingredients 1 to 10 are mixed and melted together at 60° C. Ingredient 12 is then sheared in to the dispersion.

B Ingredients 11, 13, 14, 15, 16, 17, and 18 are mixed and dissolved together and heated to 65° C.

C Part A is added to part B with stirring and homogenised for 20 minutes to give sunscreen compositions having an SPF of 15.

EXAMPLE 6

Skin Cream Emulsion Containing Vitamins

| | Ingredient | % w/w |
|---|---|---|
| 1 | Aqua | 69.5 |
| 2 | Butylene glycol | 5.0 |
| 3 | Isotridecyl salicylate | 4.0 |
| 4 | Paraffinum liquidum | 4.0 |
| 5 | Octyl methoxycinnamate | 2.0 |
| 6 | Petrolatum | 3.0 |
| 7 | Cetyl Alcohol | 2.0 |
| 8 | Glycerin | 2.0 |
| 9 | Dimethicone | 2.0 |
| 10 | Cetearyl alcohol | 1.6 |
| 11 | Sodium Ascorbyl Phosphate (Vitamin C) | 1.0 |
| 12 | Butyl methoxydibenzoylmethane | 1.0 |
| 13 | Hydroxyethylcellulose | 0.4 |
| 14 | PEG-20 stearate | 0.4 |
| 15 | Polyacrylamide | 0.4 |
| 16 | Parfum | 0.3 |
| 17 | C13-14 isoparaffin | 0.2 |
| 18 | Tocopheryl acetate (Vitamin E) | 0.15 |
| 19 | Retinyl palmitate (Vitamin A) | 0.12 |
| 20 | Tetrasodium EDTA | 0.1 |
| 21 | Citric acid | 0.08 |
| 22 | Laureth-7 | 0.055 |
| 23 | BHT | 0.0024 |
| 24 | Preservative | q.s |

Method

Stage 1

Tetrasodium EDTA and Citric acid were added to the water using a prop stirrer. The hydroxyethylcellulose was added and hydrated using a homogeniser. Butylene glycol and glycerin were then added and the bulk was heated to 70° C.

Stage 2

The oil phase (ie components 3 to 10, 12, 14 and 17) was mixed and heated to 70° C. to melt the waxes.

Stage 3

Using a homogeniser, the oil phase, including sunscreens, was added to the aqueous phase and the bulk was mixed until emulsified and stable. The emulsion was then cooled to below 35° C. using stirring.

Stage 4

The remaining raw materials, including the vitamins were added and the product was mixed using a prop stirrer until uniform. The product was made to weight using purified water.

EXAMPLE 7

Oil-in-Water Emulsion

| | Ingredient | % w/w |
|---|---|---|
| 1 | Aqua | to 100 |
| 2 | Glycerin | 5.0 |
| 3 | One or combination of the salicylates in Table 2 | 10 |
| 4 | Octyl methoxycinnimate | 3 |
| 5 | Butyl methoxydibenzoylmethane | 2 |
| 6 | Petrolatum | 3.0 |
| 7 | Cetyl alcohol | 2.0 |
| 8 | Steareth-2 | 1.5 |
| 9 | Glyceryl stearate | 1.5 |
| 10 | Steareth-21 | 1.0 |
| 11 | Sodium citrate | 0.06 |
| 12 | Citric acid | 0.02 |
| 13 | Hydroxyethyl cellulose | 0.3 |
| 14 | Tetrasodium EDTA | 0.05 |
| 15 | Preservative | qs |
| 16 | Parfum | qs |

Method

Stage 1

EDTA, citric acid, sodium citrate and glycerin are dispersed in the water using stirring. The hydroxyethyl cellulose is then added and hydrated using homogenisation for 5 minutes. This phase was then heated to 70° C.

Stage 2

The oils and waxes (ie components 3 to 10) are mixed in a separate vessel and heated to 70° C. until melted.

Stage 3

The oil phase is added to the aqueous phase and an emulsion is formed using high shear homogenisation for 10 minutes.

Stage 4

The emulsion is cooled to below 35° C. using stirring. The preservative and perfume are then added and the product is made to weight with purified water. The emulsion is stirred until cool and uniform.

EXAMPLE 8

Water-in-Oil Emulsion

| | Ingredient | % w/w |
|---|---|---|
| 1 | Aqua | to 100 |
| 2 | 1,3-Butylene glycol | 5.0 |
| 3 | Sodium chloride | 1.0 |
| 4 | One or combination of the salicylates in Table 2 | 18 |
| 5 | Sorbitan isostearate | 0.5 |
| 6 | Stearic acid | 0.05 |
| 7 | Butylated hydroxytoluene | 0.02 |

-continued

| | Ingredient | % w/w |
|---|---|---|
| 8 | Preservative | qs |
| 9 | Octyl methoxcinnimate | 2.5 |
| 10 | Butyl methoxydibenzoylmethane | 2.5 |

Method

Stage 1

Sodium chloride, butylene glycol are added to the water using stirring. This phase is heated to 70° C. while maintaining stirring.

Stage 2

The oil phase (ie components 4, 5 and 6), including the sunscreen is mixed and heated to 70° C. until melted and uniform.

Stage 3

Using high speed stirring, the aqueous phase is slowly added to the oil phase and stirred until emulsified and uniform. The emulsion is then transferred to a homogeniser and high shear was applied for 5 minutes.

Stage 4

The emulsion is cooled to below 35° C. with stirring and the preservative is added. Stirring continued until cool and uniform.

The following Examples cover the use of salicylates in shampoo, conditioner, and bathing and body type formulations.

EXAMPLE 9

Body Lotion

| | Ingredient | % w/w |
|---|---|---|
| 1 | Aqua | to 100 |
| 2 | Carbomer 940 | 0.3 |
| 3 | Sodium hydroxide | 0.028 |
| 4 | Glycerine | 5 |
| 5 | Glyceryl monostearate and polyoxyethylene | 4 |
| 6 | Stearate fatty acid ester | 2 |
| 7 | *Paraffinum liquidum* | 5 |
| 8 | Cholesterol | 5 |
| 9 | Oleyl alcohol | 2 |
| 10 | Tetrasodium EDTA | 0.05 |
| 11 | Preservative | qs |
| 12 | Octyl methoxycinnamate | 2.5 |
| 13 | Butyl methoxydibenzoylmethane | 2.5 |
| 14 | One or combination of the Salicylates in Table 2 | 10 |

Method

Stage 1

EDTA is dispersed in the water using stirring. The Carbomer is then added and hydrated using homogenisation for 30 minutes. Glycerin is then added and stirred until uniform using stirring. This phase is then heated to 70° C.

Stage 2

The oil phase is mixed in a separate vessel and heated to 70° C. until melted and uniform.

Stage 3

The oil phase is added to the aqueous phase and an emulsion is formed using high shear homogenisation for 10 minutes. Sodium hydroxide is then added and the shear is maintained for a further 5 minutes.

Stage 4

The emulsion is cooled to below 35° C. using stirring. The preservative is then added and the product is made to weight with purified water. The emulsion is stirred until cool and uniform.

EXAMPLE 10

Shampoo and Conditioner

| | Ingredient | % w/w |
|---|---|---|
| 1 | Aqua | to 100 |
| 2 | Sodium lauryl sulfate | 8 |
| 3 | Cocamidopropyl betaine | 2 |
| 4 | Ethylene glycol monostearate | 3 |
| 5 | Dimethicone | 3.5 |
| 6 | Hydroxypropyl guar hydroxypropyltrimonium chloride | 0.4 |
| 7 | Citric acid | 0.02 |
| 8 | Tetrasodium EDTA | 0.05 |
| 9 | Preservative | qs |
| 10 | Parfum | qs |
| 11 | Octyl methoxycinnamate | 1.8 |
| 12 | Butyl methoxydibenzoylmethane | 0.2 |
| 13 | One or combination of the salicylates in Table 2 | 2.0 |

Method

Stage 1

The following materials are added to the water in order with stirring: hydroxypropyl guar hydroxypropyltrimonium chloride, citric acid, tetrasodium EDTA, sodium lauryl sulfate, cocamidopropyl betaine, ethylene glycol monostearate, salicylates and octyl methoxycinnamate.

Stage 2

Maintaining stirring, the bulk is heated to 75° C. Once uniform, dimethicone is added and dispersed. The bulk is then cooled with constant stirring to below 35° C.

Stage 3

The preservative and perfume are added and the product is made to weight with purified water. The product is stirred until cool and uniform.

EXAMPLE 11

Shampoo

| | Ingredient | % w/w |
|---|---|---|
| 1 | Aqua | to 100 |
| 2 | Sodium lauryl sulphate | 7.8 |
| 3 | Sodium chloride | 0.8 |
| 4 | Cocamidopropyl betaine | 0.75 |
| 5 | Glycol distearate | 0.8 |
| 6 | Laureth-3 | 2 |
| 7 | Preservative | qs |
| 8 | Parfum | qs |

-continued

| | Ingredient | % w/w |
|---|---|---|
| 9 | Octyl methoxycinnamate | 1.8 |
| 10 | Butyl methoxydibenzoylmethane | 0.2 |
| 11 | One or combination of the salicylates in Table 2 | 2 |

Method

Stage 1

The following materials are added to the water in order with stirring: sodium lauryl sulphate, sodium chloride, laureth-3, cocamidopropyl betaine, octyl methoxycinnamate and salicylates.

Stage 2

Maintaining stirring, the bulk is heated to 65° C. Glycol distearate is then added and dispersed. Once uniform, the bulk was cooled with constant stirring to below 35° C.

Stage 3

The preservative and perfume are added and the product is made to weight with purified water. The product is stirred until cool and uniform and the pearl had set up.

EXAMPLE 12

Hair Conditioner

| | Ingredient | % w/w |
|---|---|---|
| 1 | Aqua | to 100 |
| 2 | Cetyl alcohol | 4 |
| 3 | Cocamide MEA | 2 |
| 4 | Stearamidopropyl dimethylamine | 1 |
| 5 | Centrimonium chloride | 0.5 |
| 6 | Citric acid | 0.02 |
| 7 | Lactic acid | 0.4 |
| 8 | hydroxyethyl cellulose | 0.5 |
| 9 | Tetrasodium EDTA | 0.05 |
| 10 | Preservative | qs |
| 11 | Parfum | qs |
| 12 | Octyl methoxycinnamate | 1.8 |
| 13 | Butyl methoxydibenzoylmethane | 0.2 |
| 14 | One or combination of the salicylates in Table 2 | 3 |

Method

Stage 1

EDTA, citric acid and lactic acid were added to the water and dispersed with stirring. The hydroxyethyl cellulose was added and hydrated using a homogeniser for 5 minutes.

The other materials were added to the water in the order shown above (excluding the parfum and preservative, including salicylates and octyl methoxycinnimate) with stirring. With constant stirring, the bulk was heated to 70° C. until all materials were dispersed, melted and uniform.

Stage 2

The product was cooled to below 35° C. using stirring. The preservative and perfume were then added and the product was made to weight with purified water. The product was then stirred until cool and uniform.

EXAMPLE 13

Oil in Water Emulsion

| | Ingredient | % w/w |
|---|---|---|
| 1 | One or combination of the salicylates in Table 2 | 10 |
| 2 | Octyl Salicylate | 2.5 |
| 3 | Butylmethoxy dibenzoyl methane | 4.0 |
| 4 | Octocrylene | 3.0 |
| 5 | Octyl butamido triazone | 0.5 |
| 6 | C12-C15 alkyl benzoate | 8.0 |
| 7 | Dimethicone | 2.0 |
| 8 | Microcrystalline Wax | 2.0 |
| 9 | Trimethylpentanediol/adipic acid/glycerin crosspolymer | 10 |
| 10 | DL-A-Tocopheryl Acetate | 1.0 |
| 11 | PVP/Hexadecene Copolymer | 1.75 |
| 12 | Butylated Hydroxytoluene BP | 0.05 |
| 13 | Glyceryl-3 Glucose Distearate | 2.0 |
| 14 | Acrylates/Vinyl Ester Copolymer | 0.1 |
| 15 | Sequestrene NA4 | 0.02 |
| 16 | 1,3-Butylene Glycol | 5 |
| 17 | Sorbithom TEP | 0.5 |
| 18 | Caustic Potash Soln 45% w/w | 0.06 |
| 19 | Preservative | qs |
| 20 | Water | qs |

Method
A Ingredients 1 to 14 are mixed and heated to 75° C.
B Ingredients 15-20 are mixed and heated to 75° C.
C Part A is added to part B with stirring
D Homogenise for 15 minutes to give sunscreen compositions of SPF 30

EXAMPLE 14

Oil in Water Emulsion

| | Ingredient | % w/w |
|---|---|---|
| 1 | One or combination of the Salicylates in Table 2 | 10 |
| 2 | Octyl Salicylate | 2.5 |
| 3 | Butylmethoxy dibenzoyl methane | 4.0 |
| 4 | Octocrylene | 3.0 |
| 5 | Octyl butamido triazone | 0.5 |
| 6 | C12-C15 alkyl benzoate | 8.0 |
| 7 | Dimethicone | 2.0 |
| 8 | Microcrystalline Wax | 2.0 |
| 9 | Titanium Dioxide | 0.3 |
| 10 | DL-A-Tocopheryl Acetate | 1.0 |
| 11 | PVP/Hexadecene Copolymer | 1.75 |
| 12 | Butylated Hydroxytoluene BP | 0.05 |
| 13 | Glyceryl-3 Glucose Distearate | 2.0 |
| 14 | Acrylates/Vinyl Ester Copolymer | 0.1 |
| 15 | Sequestrene NA | 0.02 |
| 16 | 1,3-Butylene Glycol | 5 |
| 17 | PVP/dimethiconoylacrylate/polycarbomyl/polyglycol ester | 2.0 |
| 18 | Caustic Potash Soln 45% w/w | 0.06 |
| 19 | Preservative | qs |
| 20 | Water | qs |

Method
A Ingredients 1 to 14 are mixed and heated to 75° C.
B Ingredients 15-20 are mixed and heated to 75° C.
C Part A is added to part B with stirring
D Homogenise for 15 minutes to give sunscreen compositions of SPF 30

EXAMPLE 15

Sun Oil

|   | Ingredient | % |
|---|---|---|
| 1 | Sunflower oil | 30.58 |
| 2 | A salicylate ester from Table 2 | 4.00 |
| 3 | Cyclotetrasiloxane | 22.92 |
| 4 | Octyl stearate | 20.37 |
| 5 | Paraffin | 10.18 |
| 6 | Cyclopentasiloxane | 7.64 |
| 7 | Octyl dimethyl PABA | 2.24 |
| 8 | Apricot kernel oil | 0.51 |
| 9 | Butyl methoxydibenzoylmethane | 0.51 |
| 10 | Coconut oil | 0.51 |
| 11 | Perfume | 0.3034 |
| 12 | Tocopheryl acetate | 0.20 |
| 13 | BHA | 0.04 |

Method

Heat all the ingredients apart from perfume to 65° C. and mix to ensure homogenity. Force cool the oil dispersion to room temperature and add the perfume Examples 16 to 18 are further formulations of the invention, illustrating the cosmetic use of stabilised debenzoylmethanes to protect the skin and hair from UV damage.

EXAMPLE 16

Eye Cream

| Ingredient | % |
|---|---|
| Aqua | to 100 |
| Butylene glycol | 6 |
| *Paraffinum liquidum* | 5 |
| Octyl methoxycinnamate | 4 |
| Dimethicone | 2 |
| Petrolutum | 2 |
| Cetearyl octanoate | 1.8 |
| Cetearyl alcohol | 1.6 |
| Glyceryl stearate | 1.5 |
| Cetyl alcohol | 1 |
| *Prunus dulcis* | 1 |
| Glycerin | 0.57 |
| Hydrogenated vegetable glycerides citrate | 0.5 |
| Tocopheryl acetate | 0.5 |
| Bisabolol | 0.475 |
| Panthenol | 0.45 |
| Sodium phosphate | 0.42 |
| PEG-20 stearate | 0.4 |
| Isopropyl myristate | 0.2 |
| Carbomer | 0.15 |
| PEG-12 isostearate | 0.125 |
| Allantoin | 0.1 |
| Tetrasodium EDTA | 0.1 |
| Lactic acid | 0.088 |
| Disodium phophate | 0.083 |
| Potassium hydroxide | 0.051 |
| One or combination of the salicylates in Table 2 | 10.0 |
| Butylmethoxy dibenzoyl methane | 2.9 |
| Octyl methoxycinnamate | 1.9 |
| Preservative | q.s |

Method

Stage 1

Into the water, citric acid, EDTA, sodium phosphate, disodium phosphate and lactic acid are added and dispersed. Using a homogeniser, carbomer is added and hydrated. The aqueous phase is then heated to 70° C.

Stage 2

The paraffinum liquidum, octyl methoxycinnamate, dimethicone, petrolatum, cetearyl octanoate, cetearyl alcohol, glyceryl stearate, cetyl alcohol, hydrogenated vegetable glycerides citrate, tocopheryl acetate, PEG-20 stearate, isopropyl myristate, salicylate, dibenzoyl methane and PEG-12 isostearate are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials are then added and mixed. The product is then made to weight using purified water and is stirred until uniform.

EXAMPLE 17

Foundation

| Ingredient | % |
|---|---|
| Aqua | to 100 |
| Butylene glycol | 9.8 |
| Cetearyl isononanoate | 4.9 |
| Dimethicone | 3.2 |
| Glycerin | 1.96 |
| Silica | 1.9 |
| Caprylic/capric triglyceride | 1.67 |
| *Paraffinum liquidum* | 1.67 |
| Petrolatum | 1.67 |
| Hydrogenated coco-glycerides | 1.67 |
| Cetearyl octanoate | 1.5 |
| Cetearyl alcohol | 1.35 |
| Octyl methoxycinnamate | 1.28 |
| Talc | 1 |
| Glyceryl stearate | 0.95 |
| PEG-100 stearate | 0.9 |
| Butyl methoxydibenzoylmethane | 0.6 |
| Saccharide isomerate | 0.54 |
| Lactic acid | 0.45 |
| Sodium polyacrylate | 0.45 |
| Boron nitride | 0.42 |
| Sodium PCA | 0.4 |
| *Borago officinalis* | 0.4 |
| Tocopheryl acetate | 0.4 |
| PVP/hexadecene copolymer | 0.4 |
| PEG-20 stearate | 0.33 |
| Glycolic acid | 0.2 |
| Sodium stearoyl lactylate | 0.2 |
| Isopropyl myristate | 0.17 |
| Polyaminopropyl biguanide | 0.16 |
| Tetrasodium EDTA | 0.1 |
| Xanthan gum | 0.1 |
| Citric acid | 0.06 |
| Alcohol denat. | 0.04 |
| Lecithin | 0.037 |
| Preservative | q.s |
| One or combination of the salicylates in Table 2 | 10.0 |
| Butylmethoxy dibenzoyl methane | 2.9 |
| Octyl methoxycinnamate | 1.9 |

Method

Stage 1

Into the water, citric acid, EDTA and lactic acid are added and dispersed. Xanthan gum is pre-dispersed in butylene glycol and is added to the bulk. The aqueous phase is then heated to 70° C.

Stage 2

The cetearyl isononanoate, dimethicone, silica, PVP/hexadecene copolymer, capryliclcapric triglyceride, paraffinum liquidum, petrolatum, hydrogenated coco-glycerides, cetearyl octanoate, cetearyl alcohol, octyl methoxycinnamate, talc, glyceryl stearate, PEG-100 stearate, butyl methoxydibenzoylmethane, borago officinalis, tocopheryl acetate, sodium stearoyl lactylate, isopropyl myristate, salicylate, dibenzoyl methane and lecithin oil phase are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, are then added and mixed. The product is then made to weight using purified water and is stirred until uniform.

EXAMPLE 18

Lipstick

| Ingredient | % |
| --- | --- |
| *Ricinus communis* | 15 |
| Octyldodecanol | 10 |
| Pentaerythrityl tetracaprylate/caprate | 10 |
| Mica | 10 |
| Bis-diglyceryl caprylate/caprate/isostearate/Stearate/hydroxystearate adipate | 7.5 |
| Paraffin | 5 |
| *Cera microcristallina* | 5 |
| Propylene glycol | 2 |
| Hydrogenated castor oil | 2 |
| *Candelilla cera* | 1 |
| Carnauba | 1 |
| Synthetic wax | 1 |
| *Butyrospermum parkii* | 1 |
| Titanium dioxide | 0.5 |
| Tocopheryl acetate | 0.2 |
| Polyquaternium-37 | 0.2 |
| Red colour | q.s |
| One or combination of the salicylates in Table 2 | 10.0 |
| Butylmethoxy dibenzoyl methane | 2.9 |
| Octyl methoxycinnamate | 1.9 |

Method

The materials are mixed in a vessel and heated to 85° C. until melted and uniform. The product is cooled to below 70° C. The product poured into a suitable container and allowed to cool to room temperature to set.

Examples 19 to 22 are further examples of compositions according to the invention, illustrating toiletry products designed to protect the hair and skin from UV damage.

EXAMPLE 19

UV Protective Body Wash

| Ingredient | % |
| --- | --- |
| Aqua | to 100 |
| Sodium lauryl sulfate | 20 |
| Cocamidopropyl betaine | 1.5 |
| Sodium chloride | 0.2 |
| PEG-6 Cocamide | 1 |

-continued

| Ingredient | % |
| --- | --- |
| Dipropylene glycol | 0.25 |
| PEG-18 glyceryl oleate/cocoate | 0.5 |
| PEG-40 hydrogenated castor oil | 0.5 |
| Polyquaternium-7 | 0.04 |
| PEG-7 glyceryl cocoate | 0.5 |
| Tetrasodium EDTA | 0.02 |
| Preservative | q.s. |
| Parfum | q.s. |
| One or a combination of the salicylates in Table 2 | 5 |
| Butylmethoxy dibenzoyl methane | 2 |
| Octyl methoxycinnamate | 1 |

Method

Stage 1

The following materials were added to the water in order with stirring: (in sample 1, polyquaternium-7 was added first) Tetrasodium EDTA, Sodium lauryl sulfate, sodium chloride, PEG-6, dipropylene glycol, PEG-18, PEG-40, PEG-7, cocamidopropyl betaine Stage 2

Maintaining stirring, the bulk was heated to 65° C. Once uniform, the bulk was cooled with constant stirring to below 35° C.

Stage 3

The preservative, solvent, sunscreens and perfume were added and the product was made to weight with purified water. The product was stirred until cool and uniform.

EXAMPLE 20

UV Protective Conditioning Shampoo

| Ingredient | % |
| --- | --- |
| Aqua | to 100 |
| Alpha olefin sulfonate | 25 |
| Cocamide DEA | 2 |
| Lauramide DEA | 1 |
| Oleamide MIPA | 1.5 |
| Cocamidopropyl betaine | 2 |
| Oleth-3 phosphate | 0.1 |
| Lauric acid | 0.25 |
| Sodium chloride | 0.25 |
| Preservative | q.s |
| Parfum | q.s |
| One or a combination of the salicylates in Table 2 | 5 |
| Butylmethoxy dibenzoyl methane | 2 |
| Octyl methoxycinnamate | 1 |

Method

Stage 1

The following materials were added to the water in order with stirring: Alpha olefin sulfonate, cocamide DEA, lauramide DEA, oleamide MIPA, cocamidopropyl betaine, lauric acid, oleth-3 phosphate.

Stage 2

Maintaining stirring, the bulk was heated to 65° C. Once uniform, the bulk was cooled with constant stirring to below 35° C.

Stage 3

The preservative, solvent, sunscreen and perfume were added and the product was made to weight with purified water. The product was stirred until cool and uniform.

EXAMPLE 21

UV Protective Hair Conditioner

| Ingredient | % |
| --- | --- |
| Aqua | to 100 |
| Cetyl alcohol | 4 |
| Cocamide MEA | 2 |
| Stearamidopropyl dimethylamine | 1 |
| Centrimonium chloride | 0.5 |
| Citric acid | 0.02 |
| Lactic acid | 0.4 |
| Hydroxyethyl cellulose | 0.5 |
| Tetrasodium EDTA | 0.05 |
| Preservative | q.s |
| Parfum | q.s |
| One or a combination of the salicylates in Table 2 | 5 |
| Butylmethoxy dibenzoyl methane | 2 |
| Octyl methoxycinnamate | 1 |

Method

Stage 1

EDTA, citric acid and lactic acid were added to the water and dispersed with stirring. In sample 1, the hydroxyethyl cellulose was added and hydrated using a homogeniser for 5 minutes.

The other materials were added to the water in the order shown above down to parfum with stirring. With constant stirring, the bulk was heated to 70° C. until all materials were dispersed, melted and uniform.

Stage 2

The product was cooled to below 35° C. using stirring. The preservative, solvent, sunscreens and perfume were then added and the product was made to weight with purified water. The product was then stirred until cool and uniform.

EXAMPLE 22

Hair Gel

| Ingredient | % |
| --- | --- |
| Aqua | to 100 |
| Carbomer 940 | 0.35 |
| Glycerin | 0.5 |
| Tetrasodium EDTA | 0.05 |
| Potassium Hydroxide | 0.06 |
| Preservative | q.s |
| One or a combination of the salicylates in Table 2 | 5 |
| Butylmethoxy dibenzoyl methane | 2 |
| Octyl methoxycinnamate | 1 |

Method

Stage 1

EDTA was dispersed in the water using stirring, the Carbomer was then added and hydrated using homogenisation for 30 minutes.

Glycerin was then added and mixed until uniform using stirring.

Stage 2

Sample 2 was cooled to below 35° C. using stirring. The preservative, solvent and sunscreens were then added and made to weight with purified water. The gel was stirred until cool and uniform.

Examples 23 to 26 are further examples of formulations according to the invention, illustrating the use of stabilised dibenzoylmethanes to protect the formula itself from UV degradation.

EXAMPLE 23

UV Protective Body Wash

| Ingredient | % |
| --- | --- |
| Aqua | to 100 |
| Sodium lauryl sulfate | 20 |
| Cocamidopropyl betaine | 1.5 |
| Sodium chloride | 0.2 |
| PEG-6 Cocamide | 1 |
| Dipropylene glycol | 0.25 |
| PEG-18 glyceryl oleate/cocoate | 0.5 |
| PEG-40 hydrogenated castor oil | 0.5 |
| Polyquaternium-7 | 0.04 |
| PEG-7 glyceryl cocoate | 0.5 |
| Tetrasodium EDTA | 0.02 |
| Preservative | q.s |
| Parfum | q.s |
| One or a combination of the salicylates in Table 2 | 5 |
| Butylmethoxy dibenzoyl methane | 2 |
| Octyl methoxycinnamate | 1 |

Method

Stage 1

The following materials were added to the water in order with stirring: (in sample 1, polyquaternium-7 was added first) Tetrasodium EDTA, Sodium lauryl sulfate, sodium chloride, PEG-6, dipropylene glycol, PEG-18, PEG-40, PEG-7, cocamidopropyl betaine Stage 2

Maintaining stirring, the bulk was heated to 65° C. Once uniform, the bulk was cooled with constant stirring to below 35° C.

Stage 3

The preservative, solvent, sunscreens and perfume were added and the product was made to weight with purified water. The product was stirred until cool and uniform.

EXAMPLE 24

UV Protective Conditioning Shampoo

| Ingredient | % |
| --- | --- |
| Aqua | to 100 |
| Alpha olefin sulfonate | 25 |
| Cocamide DEA | 2 |
| Lauramide DEA | 1 |
| Oleamide MIPA | 1.5 |

-continued

| Ingredient | % |
| --- | --- |
| Cocamidopropyl betaine | 2 |
| Oleth-3 phosphate | 0.1 |
| Lauric acid | 0.25 |
| Sodium chloride | 0.25 |
| Preservative | q.s |
| Parfum | q.s |
| One or a combination of the salicylates in Table 2 | 5 |
| Butylmethoxy dibenzoyl methane | 2 |
| Octyl methoxycinnamate | 1 |

Method

Stage 1

The following materials were added to the water in order with stirring: Alpha olefin sulfonate, cocamide DEA, lauramide DEA, oleamide MIPA, cocamidopropyl betaine, lauric acid, oleth-3 phosphate.

Stage 2

Maintaining stirring, the bulk was heated to 65° C. Once uniform, the bulk was cooled with constant stirring to below 35° C.

Stage 3

The preservative, solvent, sunscreens and perfume were added and the product was made to weight with purified water. The product was stirred until cool and uniform.

EXAMPLE 25

UV Protective Hair Conditioner

| Ingredient | % |
| --- | --- |
| Aqua | to 100 |
| Cetyl alcohol | 4 |
| Cocamide MEA | 2 |
| Stearamidopropyl dimethylamine | 1 |
| Centrimonium chloride | 0.5 |
| Citric acid | 0.02 |
| Lactic acid | 0.4 |
| Hydroxyethyl cellulose | 0.5 |
| Tetrasodium EDTA | 0.05 |
| Preservative | q.s |
| Parfum | q.s |
| One or a combination of the salicylates in Table 2 | 5 |
| Butylmethoxy dibenzoyl methane | 2 |
| Octyl methoxycinnamate | 1 |

Method

Stage 1

EDTA, citric acid and lactic acid were added to the water and dispersed with stirring. In sample 1, the hydroxyethyl cellulose was added and hydrated using a homogeniser for 5 minutes.

The other materials were added to the water in the order shown above down to perfum with stirring. With constant stirring, the bulk was heated to 70° C. until all materials were dispersed, melted and uniform.

Stage 2

The product was cooled to below 35° C. using stirring. The preservative solvent, sunscreens and perfume were then added and the product was made to weight with purified water. The product was then stirred until cool and uniform.

EXAMPLE 26

Hair Gel

| Ingredient | % |
| --- | --- |
| Aqua | to 100 |
| Carbomer 940 | 0.35 |
| Glycerin | 0.5 |
| Tetrasodium EDTA | 0.05 |
| Potassium Hydroxide | 0.06 |
| Preservative | q.s |
| One or a combination of the salicylates in Table 2 | 5 |
| Butylmethoxy dibenzoyl methane | 2 |
| Octyl methoxycinnamate | 1 |

Method

Stage 1

EDTA was dispersed in the water using stirring., the Carbomer was then added and hydrated using homogenisation for 30 minutes.

Glycerin was then added and mixed until uniform using stirring.

Stage 2

Sample 2 was cooled to below 35° C. using stirring. The preservative, solvent, sunscreens was then added and made to weight with purified water. The gel was stirred until cool and uniform.

The invention claimed is:

1. A personal care composition containing a dibenzoylmethane sunscreening agent exhibiting reduced degradation properties comprising:
   a) at least one dibenzoylmethane sunscreening agent; and
   b) a salicylate ester selected from the group consisting of isodecyl salicylate and isotridecyl salicylate in an amount sufficient to stabilize the at least one dibenzoylmethane sunscreening agent.

2. A composition as claimed in claim 1, wherein the dibenzoylmethane sunscreening agent is selected from the group consisting of 4-(1,1-dimethylethyl)-4'-methoxydibenzoyl methane and 4-isopropyldibenzoylmethane.

3. A composition as claimed in claim 2, wherein the dibenzoylmethane sunscreening agent is 4-(1,1-dimethylethyl)-4'-methoxydibenzoyl methane.

4. A composition as claimed in claim 1, further comprising, in addition to the dibenzoylmethane sunscreening agent(s), at least one additional sunscreening agent.

5. A composition as claimed in claim 4, wherein the at least one additional sunscreening agent includes an inorganic sunscreening agent.

6. A composition as claimed in claim 5, wherein the inorganic sunscreening agent is selected from the group consisting of microfine titanium dioxide, microfine zinc oxide and boron nitride.

7. A composition as claimed in claim 4, wherein the at least one additional sunscreening agent includes an organic sunscreening agent.

8. A composition as claimed in claim 7, wherein the organic sunscreening agent is selected from the group consisting of:

a) p-aminobenzoic acid or ester sunscreening agents;
b) methoxycinnamate esters;
c) benzophenones;
d) 2-phenylbenzimidazole-5-sulfonic acid and disodium phenyl dibenzimidazole tetrasulfonate and terphthalylidene dicamphor sulfonic acid;
e) alkyl-β,β-diphenylacrylates;
f) triazines;
g) camphor sunscreening agents;
h) organic pigment sunscreening agents;
i) silicone sunscreening agents; and
k) salicylates.

9. A composition as claimed in claim 4, wherein the at least one additional sunscreening agent is present in an amount of 0.1 to 10% by weight of the composition.

10. A composition as claimed in claim 1, wherein the composition contains a total of 0.05 to 20% by weight of sunscreening agent(s).

11. A composition as claimed in claim 1, which is intended to be applied to the skin or hair to protect the skin or hair from the deleterious effects of exposure to UV radiation, and in which the total amount of sunscreening agent(s) that are present is in the range 0.5 to 10% by weight.

12. A composition as claimed in claim 1, in which the sunscreening agent(s) are present to protect the composition from the deleterious effects of exposure to UV radiation, and the total amount of sunscreening agent(s) present is less than 1% by weight of the total composition.

13. A composition as claimed in claim 1, which contains a total of 0.05 to 10% of dibenzoylmethane by weight of the total composition.

14. A composition as claimed in claim 1, which is intended to be applied to the skin or hair to protect the skin or hair from the deleterious effects of exposure to UV radiation, and in which the amount of dibenzoylmethane present is in the range 0.5 to 10%.

15. A composition as claimed in claim 1, in which the dibenzoylmethane is present to protect the composition from the deleterious effects of exposure to UV radiation, and the amount of dibenzoylmethane that is present is less than 1% by weight of the total composition.

16. A composition as claimed in claim 1, wherein the composition contains 0.1 to 30% by weight of the salicylate ester of formula I.

17. A composition as claimed in claim 1, wherein the composition contains 1 to 25% by weight of the salicylate ester of formula I.

18. A composition as claimed in claim 17, wherein the composition contains 4 to 20% by weight of the salicylate ester of formula I.

19. A composition as claimed in claim 1, which is an aqueous or oily solution or dispersion or emulsion.

20. A composition as claimed in claim 19, which is an oil-in-water emulsion.

21. A composition as claimed in claim 19, which is a water-in-oil emulsion.

22. A composition as claimed in claim 20, which comprises one or more of the following
a) a hydrocarbon oil;
b) a wax;
c) a natural oil;
d) a silicone oil;
e) a fatty acid ester;
f) a fatty alcohol; and
g) mixtures thereof.

23. A composition as claimed in claim 20, wherein the oil phase of the emulsion comprises from 5 to 30% by weight of the composition.

24. A composition as claimed in claim 21, wherein the oil phase comprises 5 to 40% by weight of the composition.

25. A composition as claimed in claim 20, which further comprises one or more emulsifiers selected from the group consisting of:
a) sesquioleates;
b) ethoxylated esters of natural oils;
c) silicone emulsifiers;
d) anionic emulsifiers;
e) ethoxylated fatty alcohols;
f) sorbitan esters;
g) ethoxylated sorbitan esters;
h) ethoxylated fatty acid esters;
i) ethoxylated mono-, di-, and tri-glycerides;
j) non-ionic self-emulsifying waxes;
k) ethoxylated fatty acids; and
l) methylglucose esters.

26. A composition as claimed in claim 25, wherein the amount of emulsifier present in the composition is in the range 1 to 10%.

27. A method of protecting the skin or hair from exposure to UV radiation, which method comprises administering to the skin or hair of an animal or human in need thereof a personal care composition containing a dibenzoylmethane sunscreening agent exhibiting reduced degradation properties comprising:
I. at least one dibenzoylmethane sunscreening agent; and
II. a salicylate ester selected from the group consisting of isodecyl salicylate and isotridecyl salicylate in an amount sufficient to stabilize the at least one dibenzoylmethane sunscreening agent.

28. A method of reducing degradation of a dibenzoylmethane sunscreening agent in a personal care composition containing at least one dibenzoylmethane sunscreening agent, the method comprising adding to the personal care composition a photostabilizing amount of a salicylate ester selected from the group consisting of isodecyl salicylate and isotridecyl salicylate.

* * * * *